United States Patent [19]

Zhao et al.

[11] Patent Number: 5,567,607
[45] Date of Patent: Oct. 22, 1996

[54] METHOD OF PRODUCING TRANSGENIC ANIMALS

[75] Inventors: Xi Zhao; Tai-kin Wong, both of Saratoga, Calif.

[73] Assignee: Incell, Santa Clara, Calif.

[21] Appl. No.: 424,221

[22] Filed: Apr. 19, 1995

Related U.S. Application Data

[63] Continuation of Ser. No. 291,136, Aug. 16, 1994, abandoned, which is a continuation of Ser. No. 59,180, May 6, 1993, abandoned, which is a continuation of Ser. No. 475,726, Feb. 6, 1990, abandoned, which is a continuation-in-part of Ser. No. 215,670, Jul. 6, 1988, abandoned, which is a continuation-in-part of Ser. No. 142,320, Dec. 30, 1987, Pat. No. 4,849,355, which is a continuation of Ser. No. 689,657, Jan. 8, 1985, abandoned, which is a continuation-in-part of Ser. No. 315,944, Oct. 28, 1981, abandoned.

[51] Int. Cl.$^6$ .............. C12N 15/85; C12N 5/16; C12N 13/00
[52] U.S. Cl. .............. 435/172.1; 435/172.3; 435/320.1; 435/240.2; 435/173.6; 935/23; 935/32; 935/52; 935/53; 800/2; 800/DIG. 1; 800/DIG. 2; 800/DIG. 6
[58] Field of Search ............ 800/2, DIG. 1, 800/DIG. 2, DIG. 3, DIG. 4; 435/172.3, 172.1, 320.1, 240.2, 289, 173.5, 173.6; 935/23, 32, 52, 53, 54, 50

[56] References Cited

U.S. PATENT DOCUMENTS 4,663,292  5/1987  Wong et al. ............ 435/285.2
4,870,009  9/1989  Evans et al. ............ 435/69.4

OTHER PUBLICATIONS

Robl et al. 1986 Thenogenobgy 25, 189.
Berg et al. 1984 Bioelectrochem. Bioenerget. 12, 119–133.
Uize et al. 1987 Gene 55, 339–344.
Old et al. 1985 in: *Principles of Gene Manipulation An Introduction to Genetic Engineering*. Blackwell Sci. Publ., Oxford Eng. pp. 262–265.
Hogan et al. 686 in: *Manipulating the Main Embryo. A Laboratory Manual*. Cold Spring Harbor Laboratory, NY. pp. 153–154.
Nemec et al. 1989 Theriogenology 31, 233.
*Webster's Third New International Dictionary*, 1963, G & C Marriam Company Ma. p. 740.
*Webster's II New Riverside University Dictionary*, Soukhanov et al. (ed.) 1984, Houghton Mifflin Company, Boston, MA, pp. 67 and 119–120.
Asubel et al. (eds.) 1988, in: *Current Protocols in Molecular Biology* (vol. 2), John Wiley & Sons, New York, NY, appendix p. A.2.3.

*Primary Examiner*—Christopher S. F. Low
*Attorney, Agent, or Firm*—Blakely, Sokoloff, Taylor & Zafman

[57] ABSTRACT

A method is provided for making transgenic animals by transferring DNA into embryo by subjecting the mixture of the DNA to be transferred and the embryo to an electric discharge.

13 Claims, 2 Drawing Sheets

5,567,607

METHOD OF PRODUCING TRANSGENIC ANIMALS

This is a continuation of application Ser. No. 08/291,136 (now abandoned), filed Aug. 16, 1994, which is a continuation of application Ser. No. 08/059,180 (now abandoned), filed May 6, 1993, which is a continuation of Ser. No. 07/475,726 (now abandoned), filed Feb. 6, 1990, which is a CIP of 07/215,670 (now abandoned) filed Jul. 6, 1988; which is a CIP of Ser. No. 07/142,320 filed Dec. 30, 1987, now U.S. Pat. No. 4,849,355 which is a continuation of Ser. No. 06,689,657 now abandoned, filed Jan. 8, 19985; which is a CIP of Ser. No. 06/315,944, (now abandoned) filed Oct. 28, 1981.

The present invention is a method to transfer of DNA, into embryos to produce transgenic animals. In the fields of genetic engineering, cell biology, and embryo manipulation, various chemical and mechanical methods have been developed for transferring genetic materials into cells. Chemical methods involve the use of chemicals which permeabilize the cell surface, hence facilitates the transfer of the genetic materials into cells. [For reviews, see: Gerard Venema "Bacterial Transformation" in Adv. Microbiol. Physl. (1979) 19: 245–331; George Scangos and Frank H. Ruddle "Mechanisms and Applications of DNA-mediated Gene Transfer in Mammalian Cells—A Review" in Gene (1981) 14: 1–10; O. Wesley McBride and Jane L. Peterson "Chromosome-mediated Gene Transfer in Mammalian Cells" in Ann. Rev. Genet. (1980) 14: 321–345; Jürgen Horst et al., "On Procaryotic Gene Expression in Eucaryotic Systems" in Human Genetics (1980) 54: 289–302; R. Fraley and D. Papahadjopoulos, "New Generation Liposomes; The Engineering of an Efficient Vehicle for Intracellular Delivery of Nucleic Acids" in Trends Biochem. Sci. (1981) March. pp. 77–80.] Mechanical methods involve the injection of genetic materials directly into the cells, commonly known as microinjection (For review, see: W. French Anderson and Elaine G. Diacumakos "Genetic Engineering in Mammalian Cells" in Scientific American (1981) 245: 106–121).

In procaryotic systems, the chemical methods of transferring genes are usually employed, whereas in eucaryotic systems, both the chemical and mechanical methods are used.

All available methods, however, are somewhat dependent upon both the gene which is to be transferred and the recipient cells. Methods which may be used to transfer genes into procaryotes may not work in transferring genes into eucaryotes. However, according to the present invention, a single method is provided which may be utilized to transfer genes into either procaryotic or eucaryotic cells.

According to the present invention a solution or suspension containing the DNA to be transferred and the embryo are placed in a receptacle such that one electrode contacts the solution, suspension or mixture below the surface thereof. Preferably the said electrode is located at the lowest point of the said receptacle. Juxtaposed above the surface of the solution, suspension or mixture, but not in contact therewith is a second electrode directed towards the surface of the solution, suspension or mixture. The distance between the point of the second electrode and the surface of the solution, suspension or mixture is not critical. A distance of about 0.7 cm to about 4 cm has been used.

The electrodes may be connected to a conventional electric field generator. The electric field which may be applied to the solution or suspension containing the cells and gene must be high enough to create a high electric field or electric discharge but not great enough to substantially alter or destroy the cells or the gene. Voltages from approximately 1 kilovolt to 8 kilovolts may be used.

When an electric field is applied to the gene-embryo mixture, the pulse duration of the field varies from about 1 microseconds to 200 microseconds/pulse, usually about 120 microseconds depending on the nature of the target cells. When discharge condition is employed, a pulse discharge up to about 120 microseconds/pulse is preferred. These pulses are given in about 0.2 to 3.2 second bursts at a distance of about 0.5 to 3 mm from the mixture. The number of pulses which may be applied to the solution, suspension or mixture containing DNA may vary from about $2^4$ to about $2^{11}$, depending upon the pulse width and intensity (amplitude) and the nature of the cells. The amplitude will usually be in the range of about 1–8 kV. The preferred number of pulses is about $2^6$ to $2^9$ at about 30 to 108 μS/pulse Preferably about $2^9$ pulses are used with a width of 120 μS and voltage intensity of about 3 kV.

Figure 1:
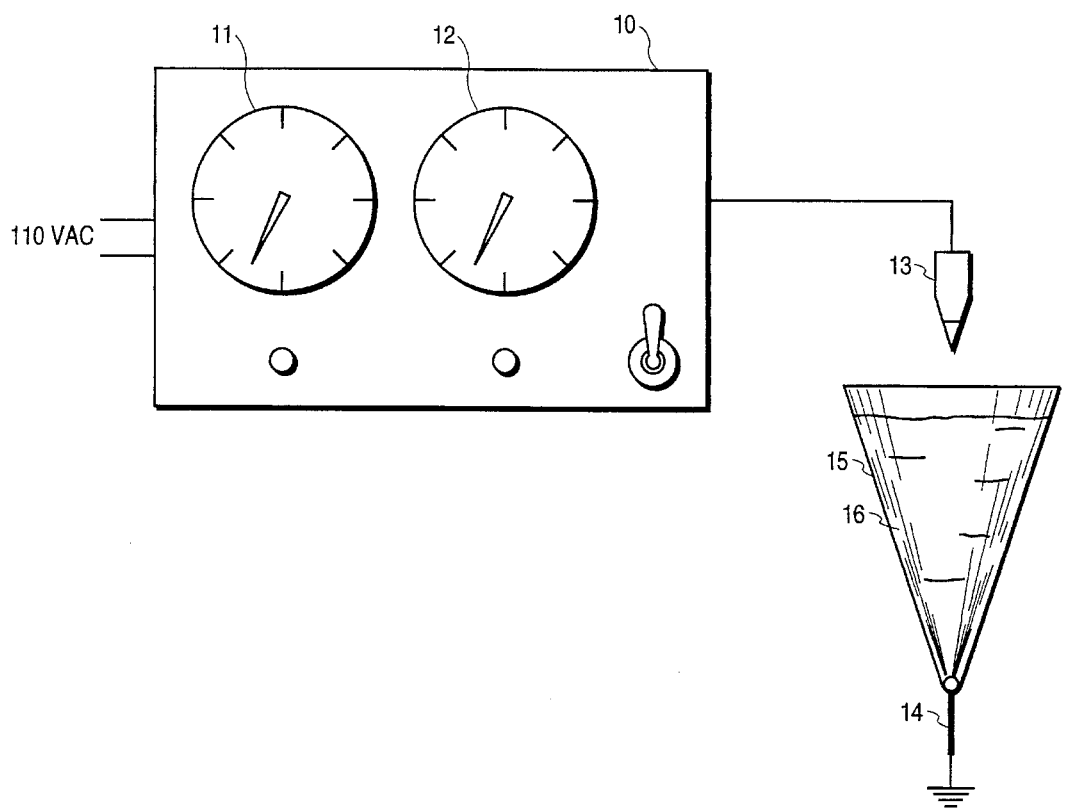
FIG. 1 is a diagram of an apparatus employed in the preferred embodiment of the invention.

Referring to FIG. 1, there is shown a conventional electric field generator 10 having a control and monitoring means 11 for applying field or pulse and an intensity control and measuring means 12 for voltage. Such a conventional generator is available, for example, from Andy Hish Associates, Van Nuys, Model Number ESD255 Electrostatic Discharge Generator with probe P255-1. Probe 13 is connected to said generator 10 and vertically disposed above vial receptacle 15. At the lowest point of vial receptacle 15 is located a ground electrode 14. Vial receptacle 15 contains a solution or suspension of cells and genes. As shown, vial receptacle 15 may be conical in shape and the ground electrode 14 is located at the apex thereof. Without limiting the invention to any particular theory, the shape of vial receptacle 15 may be preferred since there may be a concentration gradient of cells within the solution or suspension 16 due to the heterogeneity of the cells and in such case the gradient concentration of cells may be near the apex of vial receptacle 15. A preferred apparatus embodying the features of FIG. 1 is the BAEKON 2000, manufactured by Baekon, Inc., 20333 Merida Drive, Saratoga, Calif., and which is described in U.S. Pat. No. 4,663,292, incorporated by reference herein.

Figure 2:
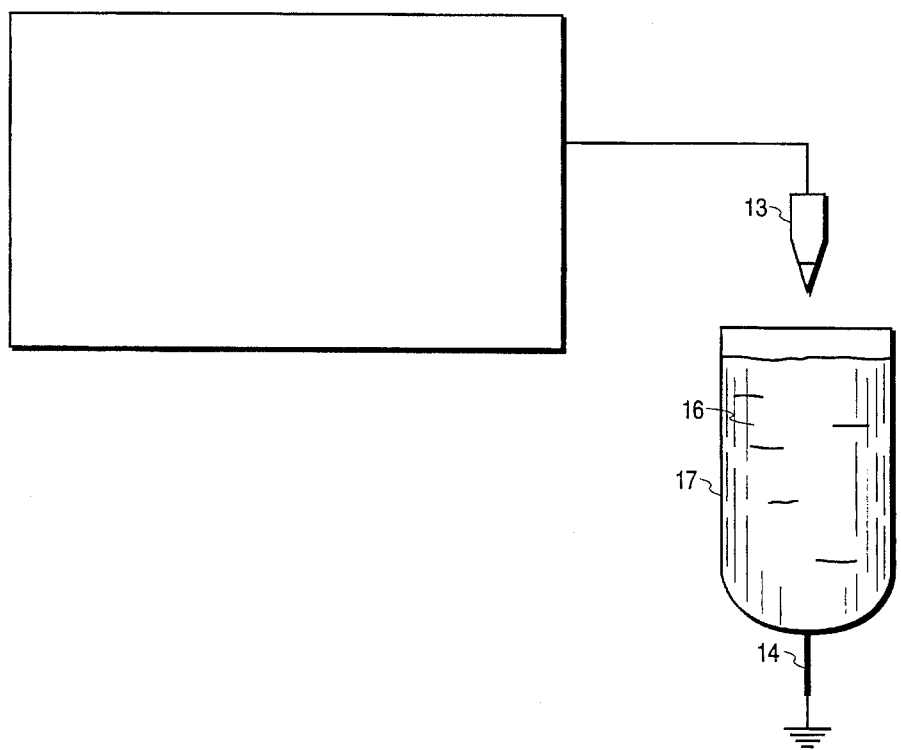
FIG. 2 is a diagram of an apparatus employed in a second embodiment of the invention.

Referring to FIG. 2 there is shown a second embodiment of the invention. FIG. 2 is similar to FIG. 1 except that receptacle 17 is a tube with a round bottom having the ground electrode located at the lowest point of the tube.

Figure 3:
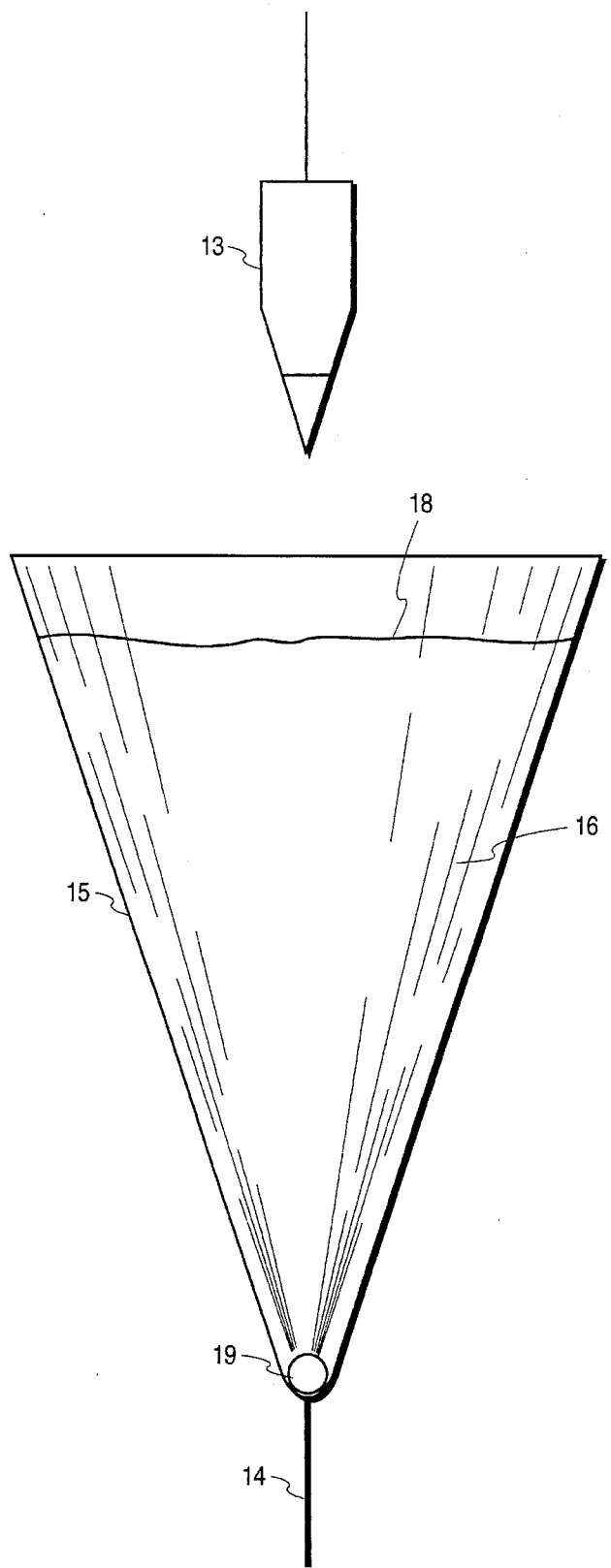
FIG. 3 is an enlarged view of a preferred receptacle shown in FIG. 1.

Referring to FIG. 3 there is shown an enlarged view of vial receptacle 15. As shown, a probe 13 is directed towards the surface 18 of the solution or suspension containing the cells and genes. Both the probe 13 and the vial 15 containing solution 16 may be exposed to the atmosphere during the experiment. It is readily apparent that the vial 15 need not be completely filled as shown in order to perform the experiment. A requirement is that the cells and gene containing solution or suspension is placed between direct discharge or electric field from probe 13 to ground electrode 14.

According to the present invention DNA, including genes, may be transferred into embryo of animals or humans. For example, growth hormone genes, insulin genes, Hepatitis B surface antigen genes, erthropoietin genes, lymphokine genes, urokinase genes, etc.

The genes which may be transferred according to the present invention may be structural genes, i.e., DNA fragments comprising the gene, or may be genes on vectors, such as, plasmid vectors, cosmid vectors, phage vectors, viral vectors, etc.

The present invention may be utilized to produce animals having improved genetic characteristics, such as the growth rate, coloration and patterning, disease resistance, drug tolerance, etc.

For purposes of illustrating the present invention the following examples are provided. However, the scope of the invention is not intended to be limited thereto.

EXAMPLE

Gene Transfer into Mouse Embryo

Into the receptacle of the Baekon 2000 Advanced Macromolecule Transfer System were mixed 100 embryos (1-cell stage) of BDF-1 strain of mouse in 100 ul of a sterilized buffer M2 comprising 94.66 mM NaCl, 4.78 mM KCl, 1.71 mM $CaCl_2$, 1.19 mM $KH_2PO_4$, 1.19 mM $MgSO_4$, 4.15 mM $NaHCO_3$, 20.85 mM Hepes, 23.28 mM Na-Lactate, 0.33 nM Na-pyruvate, 5.56 nM Glucose, 100 Unit/ml penicillin and streptomycin, 0.1% phenol red, and 10 ug of DNA of growth hormone gene from porcine. The machine was set at amplitude 3.5 kV, number of pulses at 512, pulse time at 102 uS, burst time at 0.8 sec, cycles at 5, and non-contact mode of operation with 1 mm between the positive electrode and the meniscus of the gene-embryo mixture. Two more samples were similarly treated. After exposure to the treatment, the embryos were washed twice with M2 medium, and cultured to 2-cell stage in M16 medium at 37° C. in a humidified atmosphere of 5% $CO_2$ in air. Embryos were reimplanted into pseudo-pregnant female mice. Out of a total 280 embryos in three samples, 95 baby mice were born, of which 19 showed positive integration of the DNA into the genome as detected by hybridization.

What is claimed is:

1. A method for transferring DNA into fertilized eggs of a non-human mammal, comprising: subjecting a mixture of said DNA and said fertilized eggs to pulses of an electric field for a time sufficient to effect transfer of said DNA to said fertilized eggs.

2. The method according to claim 1 wherein said electric field is provided by a first and a second electrode having a voltage between said first and said second electrode of from approximately 3 (kv) to 20 Kilovolts.

3. A method according to claim 1 wherein said DNA comprises at least one gene.

4. A method according to claim 1 wherein said DNA is transferred into said fertilized eggs on a vector.

5. A method according to claim 1 wherein said pulses comprise $2^6$ to $2^9$ pulses.

6. A method according to claim 1 wherein said electric field is maintained for a duration of from about 1 second to 90 seconds.

7. A method according to claim 1 wherein said fertilzed eggs are from a mouse.

8. A method for transferring DNA into an oocyte of a nonhuman mammal, comprising: subjecting a mixture of said DNA and said oocyte to pulses of an electric field for a time sufficient to effect transfer of said DNA to said oocyte.

9. The method according to claim 8, wherein said electric field is provided by a first and a second electrode having a voltage between said first and said second electrode of from approximately 3 to 20 kilovolts.

10. A method according to claim 8, wherein said DNA comprises at least one gene.

11. A method according to claim 8, wherein said DNA is transferred into said oocyte on a vector.

12. A method according to claim 8, wherein said pulses comprise $2^6$ to $2^9$ pulses.

13. A method according to claim 8, wherein said electric field is maintained for a duration of from about 1 second to 90 seconds.

* * * * *